United States Patent [19]

Paul

[11] Patent Number: Plant 5,413

[45] Date of Patent: Mar. 12, 1985

[54] PLUM TREE 'MR. PAUL'

[76] Inventor: Ronald Paul, 5485 E. Heaton Ave., Fresno, Calif. 93727

[21] Appl. No.: 465,876

[22] Filed: Feb. 11, 1983

[51] Int. Cl.[3] ..... A01H 5/00
[52] U.S. Cl. ..... Plt./38
[58] Field of Search ..... Plt./38

*Primary Examiner*—James R. Feyrer
*Attorney, Agent, or Firm*—Vergil L. Gerard

[57] ABSTRACT

Disclosed is a new and distinct plum tree (Mr. Paul) broadly characterized by a large, vigorous, productive and regular bearing tree, late ripening fruit which is ready for first picking the third week of July, nearly one month later than the parent plant, Queen Rosa (unpatented), which it most nearly resembles, and of good keeping and shipping quality and mild, very pleasant, sweet flavor. This plant bears the cultivar name 'Mr. Paul'.

1 Drawing Figure

The present invention relates to a plum tree and more particularly to a new and distinct variety broadly characterized by a large, vigorous, productive and regular bearing tree, late ripening fruit which is ready for first picking the third week of July, nearly one month later than the parent plant, Queen Rosa (unpatented), and otherwise generally resembling the fruit of the Queen Rosa, and of good keeping and shipping quality and mild, very pleasant, sweet flavor. The instant plant bears the cultivar name 'Mr. Paul'.

The instant variety most nearly resembles its parent plant, Queen Rosa (unpatented), developed by the U.S. Department of Agriculture, but is an improvement thereon by ripening nearly one month later than Queen Rosa, which ripens at the end of the Santa Rosa (unpatented) season, with the first picking the third week in July.

I discovered the instant variety of plum tree in a nine year old bearing commercial orchard of Queen Rosa plum trees of which I am co-owner, in Fresno County, Calif., where it appeared as a late ripening mutation. The mutation was then asexually reproduced by me by grafting onto mature plum tree stock in February, 1980. Fruit reproduced on the grafted trees in 1982. The reproductions of the plant and fruit characteristics were true to the original mutation in all respects.

The accompanying photograph shows the characteristics of the whole fruit in skin color and form, and a characteristic fruit divided at its suture plane showing the flesh color and stone.

Referring now more specifically to the pomological characteristics of this new and distinct variety of plum tree, the following has been observed under the ecological conditions prevailing near Fresno County, Calif., and was developed at full commercial maturity on July 24, 1982. All color plate identifications are by reference to Maerz and Paul Dictionary of Color, 1950 Ed.

TREE

General: Large, vigorous, very upright when young and spreading with age and crop, with shape and density determined by pruning. Productive and regular bearing.

Trunk: Medium thickness, medium surface texture. Older bark greyish color (7-C-7) with numerous lenticles.

Branches: Medium in size and surface texture. Mature one year old shoots brownish in color (15-L-8). Young shoots green (14-K-1).

Leaves: Measurements from midshoot leaves from vigorous shoots.

Size: Medium to large in size. Average length 14.2 cm. Average width 5.6 cm.

Form: Generally obovate with apex acuminate (at times cuspidate) and curved to one side.

Color: Upper leaf surface dark green (24-L-5). Lower leaf surface light green (23-E-5).

Leaf margin: Strongly crenate, often doubly crenate at midpoint to apex, singly near base, tipped with small brownish gland (15-E-11).

Petiole: Medium size, 15–19 mm long, 1–2 mm, thick. Light greenish color (21-J-1) dorsally, often tinged purple ventrally along ventral channel where exposed to sun (56-H-2).

Stem glands: Number 1 to 4. Most often 1 to 2 on petiole and 2 on base of leaf blade. Small, globose, greenish (21-G-2).

Stipules: 1 to 2 at petiole base, greenish (21-H-5). 10 to 12 mm long on mature leaves, usually persistent.

FLOWERS

Flower buds: Medium size, free from stem, plump and moderately pubescent.

Flowers: Late blooming, resemble parent plant, Queen Rosa, in color and shape.

FRUIT

Maturity: First pick third week of July. Last pick fourth week of July. Described at full commercial maturity on July 24, 1982.

Size: Uniform, large, average axial diameter 60 cm, average axial suture diameter 65 cm, average cheek diameter 68 cm.

Form: Uniform, symmetrical, nearly globose in axial aspect. Oblate in lateral aspect.

Suture: A distinct purple line (56-J-8) extending continuously from apex, generally broader (2–3 mm) at midpoint. Suture color usually darker than remainder of fruit.

Ventral surface: Smooth, rounded, no lips present.

Stem cavity: Rounded, broad and nearly oval in axial aspect. Relatively shallow, 6 to 8 mm in depth. Width 10 to 13 mm, length 10 to 13 mm.

Base: Rounded to slightly truncate. Often slightly oblique to dorsal suture.

Apex: Rounded. Tip slightly depressed. Pistil point apical, a very inconspicuous dot.

Stem: Medium length, 11 to 13 mm. Moderately thick, 2 to 2½ mm. Brownish color (13-G-8).

Skin: Medium thickness and medium texture. No observed tendency to crack. Skin is free of acidity when fruit fully mature. Tenacious to flesh. Color red (6-L-5) to purple-red (7-L-6) over 60–90% of fruit surface. Ground color yellow (17-J-1) to yellow-green (18-K-2) evident over shoulder area. Pubescence lacking. Moderate number of very small yellow flecks and dots over apex and cheeks of fruit. Flecking sparse over basal shoulder area. Moderately heavy bloom overall.

Flesh: Very light yellow-amber (11-F-1) with no red coloration bleeding into flesh from skin. Surface of pit cavity slightly darker (11-J-4).

Texture: Firm, fine, meaty, softens slowly becoming moderately juicy.

Fibers: Moderate in number, fine, tender.

Ripens: Evenly.

Aroma: Very slight.

Flavor: Good, Mild, very pleasant. Sweet.

STONE

Tenacity: Clingstone. Adheres to flesh over most of stone surface.

Size: Medium in size. Average length 23–25 mm. Average width 20–23 mm. Average thickness 10–11 mm.

Form: Very irregular. Generally oval but unsymmetrical in lateral aspect.

Ventral Edge: Often with strong wing protruding from basal shoulder to above midpoint on suture. Deep groove at base of wing (at times doubly grooved) somewhat parallel to wing edge but converging apically and basally.

Dorsal Edge: Deep groove extending from base to apex. Ridges on each side of groove very jagged and quite thin. At times pits on ridge surface extend completely through the ridge.

Base: Oval. Straight in relation to stone axis.

Sides: Heavily grooved near base with small sharp ridges extending up from the base into mid-stone area. Apex shoulder area netted with shallow pits and fine, short but sharp ridges.

Apex: Rounded with very short, sharp cuspidate tip.

Color: Buff to hazel; lighter color along wing and sutures (11-F-4), darker on sides (12-E-5). No observed tendency to split.

USE

Fresh Market, both local and long distance shipping. Keeping quality good, shipping quality good. No particular susceptibilities observed.

Having thus described and illustrated my new variety of plum tree, what is claimed is:

1. A new and distinct variety of plum tree having the cultivar name 'Mr. Paul' substantially as described and illustrated, which is characterized by a vigorous, regular bearing tree and fruit of mild, sweet, pleasant flavor, which most nearly resembles its parent plant Queen Rosa (unpatented) but is distinguished therefrom and an improvement thereon by ripening in late July, approximately a month later than Queen Rosa, and by a more attractive skin coloration, being darker color overall and having a band of purple coloration along the suture at full maturity.

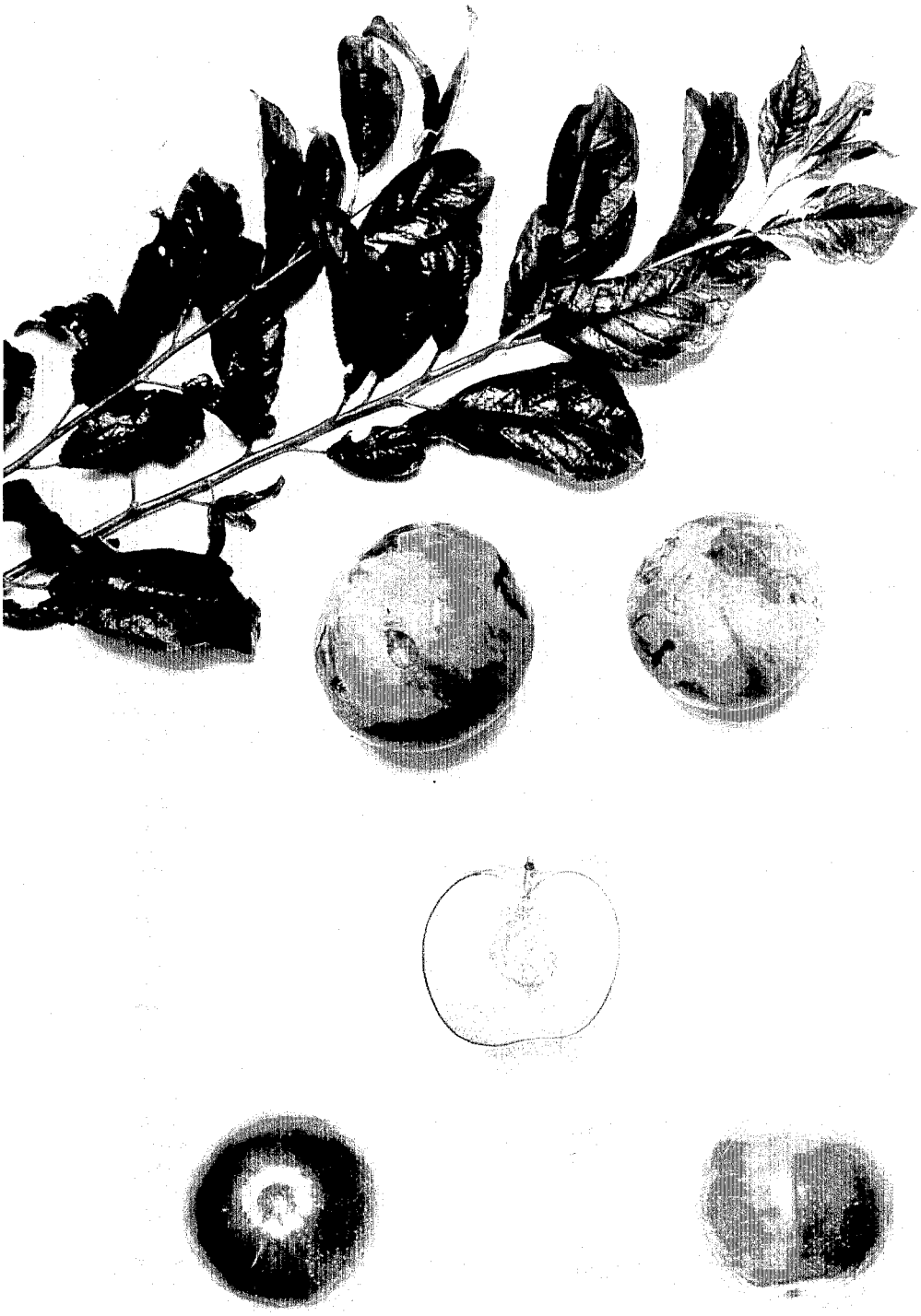

* * * * *